(12) United States Patent  
Lifshin et al.

(10) Patent No.: US 8,669,524 B2
(45) Date of Patent: Mar. 11, 2014

(54) SCANNING INCREMENTAL FOCUS MICROSCOPY

(75) Inventors: Eric Lifshin, Voorheesville, NY (US); Michael Stessin, Niskayuna, NY (US); Isaak Chagouel, Albany, NY (US)

(73) Assignee: The Reseach Foundation of State University of New York, Albany, NY (US)

( * ) Notice: Subject to any disclaimer, the term of this patent is extended or adjusted under 35 U.S.C. 154(b) by 678 days.

(21) Appl. No.: 12/911,334

(22) Filed: Oct. 25, 2010

(65) Prior Publication Data

US 2012/0097848 A1 Apr. 26, 2012

(51) Int. Cl.
*G01N 23/225* (2006.01)
*H01J 37/28* (2006.01)
*H01J 37/26* (2006.01)
*H01J 31/28* (2006.01)

(52) U.S. Cl.
CPC ............ *G01N 23/225* (2013.01); *H01J 37/263* (2013.01); *H01J 31/28* (2013.01); *H01J 31/226* (2013.01)
USPC ............................ 250/307; 250/310; 250/311

(58) Field of Classification Search
USPC ................................................. 250/306–311
See application file for complete search history.

(56) References Cited

U.S. PATENT DOCUMENTS

| 3,829,691 | A |  | 8/1974 | Hufnagel |
|---|---|---|---|---|
| 4,894,540 | A | * | 1/1990 | Komatsu ........................ 250/307 |
| 5,681,112 | A |  | 10/1997 | Kuroda et al. |
| 5,715,334 | A |  | 2/1998 | Peters |
| 5,753,913 | A |  | 5/1998 | Coene et al. |
| 5,912,993 | A |  | 6/1999 | Puetter et al. |
| 6,895,125 | B2 |  | 5/2005 | Puetter et al. |
| 7,598,492 | B1 |  | 10/2009 | Krzeczowski et al. |
| 7,605,364 | B2 |  | 10/2009 | Oosaki et al. |
| 7,915,582 | B2 | * | 3/2011 | Hirose et al. ................... 250/310 |
| 2004/0170340 | A1 |  | 9/2004 | Tipping et al. |
| 2005/0189491 | A1 |  | 9/2005 | Lewis |
| 2006/0108525 | A1 |  | 5/2006 | Nakagaki et al. |
| 2006/0293860 | A1 |  | 12/2006 | Bressler et al. |
| 2008/0067337 | A1 |  | 3/2008 | Oosaki et al. |
| 2008/0175508 | A1 |  | 7/2008 | Bando et al. |
| 2008/0283743 | A1 |  | 11/2008 | deCecco et al. |
| 2009/0110321 | A1 |  | 4/2009 | Vija et al. |
| 2009/0220129 | A1 |  | 9/2009 | Oaknin et al. |

(Continued)

OTHER PUBLICATIONS

"Deltavision Deconvolution Microscope", http://micro.salk.edu/dv/dv.html, May 21, 2010, 1 pg.

(Continued)

*Primary Examiner* — Jack Berman
(74) *Attorney, Agent, or Firm* — Brenda Birken, Esq.; Matthew M. Hulihan, Esq.; Heslin Rothenberg Farley & Mesiti P.C.

(57) ABSTRACT

Method and apparatus are provided for generating an enhanced image of an object. The method includes obtaining images of an area of an object generated using a probe of having a probe size greater than or equal to a minimum probe area size. An enhanced image of the area of the object is generated by accurately computing the emission intensities emitted from pixel areas smaller than the minimum probe size and within the area of the object. This is repeated for other areas of the object to form other enhanced images. The enhanced images are combined to form an accurate enhanced image of the object.

22 Claims, 9 Drawing Sheets

(56) References Cited

U.S. PATENT DOCUMENTS

| | | |
|---|---|---|
| 2009/0266985 A1 | 10/2009 | Nakahira et al. |
| 2010/0014732 A1 | 1/2010 | Vija et al. |
| 2010/0092086 A1 | 4/2010 | Lei et al. |
| 2010/0103253 A1 | 4/2010 | Sieckmann et al. |
| 2010/0123807 A1 | 5/2010 | Lee et al. |
| 2010/0141807 A1 | 6/2010 | Alon et al. |
| 2011/0266440 A1 | 11/2011 | Boughorbel et al. |
| 2012/0126117 A1 | 5/2012 | Nakahira et al. |

OTHER PUBLICATIONS

"The Pixon Method of Image Reconstruction", Puetter et al., Astronomical Data Analysis Software and System, VIII ASP Conference Series, vol. 172, 1999, pp. 307-316.

"BEAMETR", http://www.abeamtech.com/?dir=products/BEAMETR&pg=about, ABEAM Technologies, Jun. 23, 2010.

"FAQ", http://222.abeamtech.com/?dir=products/BEAMETR&pg=FAQ, ABEAM Technologies, Jun. 23, 2010.

"CHARIOT", http://www.abeamtech.com/?dir=products/CHARIOT&pg=about, ABEAM Technologies, Jun. 23, 2010.

"PERFORMANCE", http://www.abeamtech.com/?dir=procducts/TEMPTATION&pg=performance, Jun. 23, 2010.

Carmi E. et al., "Resolution Enhancement in MRI," Magnetic Resonance Imaging, Elseiver Science, Tarrytown, NY, US, vol. 24, No. 2, Feb. 1, 2006.

Nabeel A. Riza and Mumtaz A. Sheikh, "Liquid Lens Confocal Microscopy with Advanced Signal Processing for Higher Resolution 3D Imaging,"Medical Imaging 2009: Physics of Medical Imaging, edited by Ehsan Samei, Jiang Hsieh, Proc. of SPIE vol. 7258.

International Search Report and Written Opinion for PCT/US2011/057303 dated Apr. 11, 2012.

\* cited by examiner

SCANNING INCREMENTAL FOCUS MICROSCOPY

TECHNICAL FIELD

This invention relates generally to the imaging of objects, and more specifically to techniques for generating enhanced resolution images.

BACKGROUND OF THE INVENTION

In microscopic imaging, efforts are continually being made to achieve higher resolution microscopic images. For example, in the case of scanning probe techniques, the quest for high resolution has traditionally been addressed by finding ways to reduce the probe size while minimizing the corresponding reduction of probe current so as not to encounter serious signal to noise limitations, since the signals measured are always directly proportional to the probe current. In scanning electron microscopy (SEM), for instance, the major ways to accomplish this has been through a combination of brighter sources, such as the use of field emission and Schottky sources, as well as improvements in electron optical design. Similar developments are taking place in other techniques such as scanning transmission electron microscopy (STEM), auger electron microscopy, focused ion beam (FIB), secondary ion mass spectrometry (SIMS), Rutherford backscattering (RBS), proton induced x-ray emission (PIXE), and other x-ray probing techniques including x-ray photoelectron spectroscopy (XPS).

All of these techniques, both scanning and non-scanning, often share the common goals of high spatial resolution, distinguishable levels of contrast and low signal to noise ratios. All of these factors are critical to obtaining useful images. For example, with little or no contrast, even when high resolution is possible, fine detail in an image will not be seen. Similarly, if the signal is very weak, even when high resolution is possible and the contrast is adequate, then noise may still limit the ability to obtain high resolution images of discernable features.

Many current developments in the scanning probe techniques have concentrated on probe size minimization coupled with attempts to choose experimental conditions such that the signal measured comes from a pixel corresponding in size to the probe size. However, because of the strong relationships that exist between resolution, contrast and signal to noise ratio in scanning probe techniques, reducing probe size becomes more prohibitive. Microscopes with extremely small probe sizes are expensive and require considerable care and expertise to maintain due to instrument design and environmental considerations such as mechanical vibrations, contamination, stray fields, and thermal variations, which can all undermine and limit the quality of results. A technique is needed that can provide accurate signal values for resolutions higher than those limited by probe size.

BRIEF SUMMARY OF THE INVENTION

The shortcomings of the prior art are overcome and advantages are provided through the provision of an improved method for generating an image. The method includes, for instance, obtaining images of an area of an object generated using probes equal to or greater than a minimum probe size area, and generating from the images an enhanced image, the generation of the enhanced image comprising computing an emission intensity emitted from a pixel area of the area of the object, the pixel area being smaller than the minimum probe area size.

Systems and computer program products relating to one or more aspects of the present invention are also described and claimed herein.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION

Figure 1:
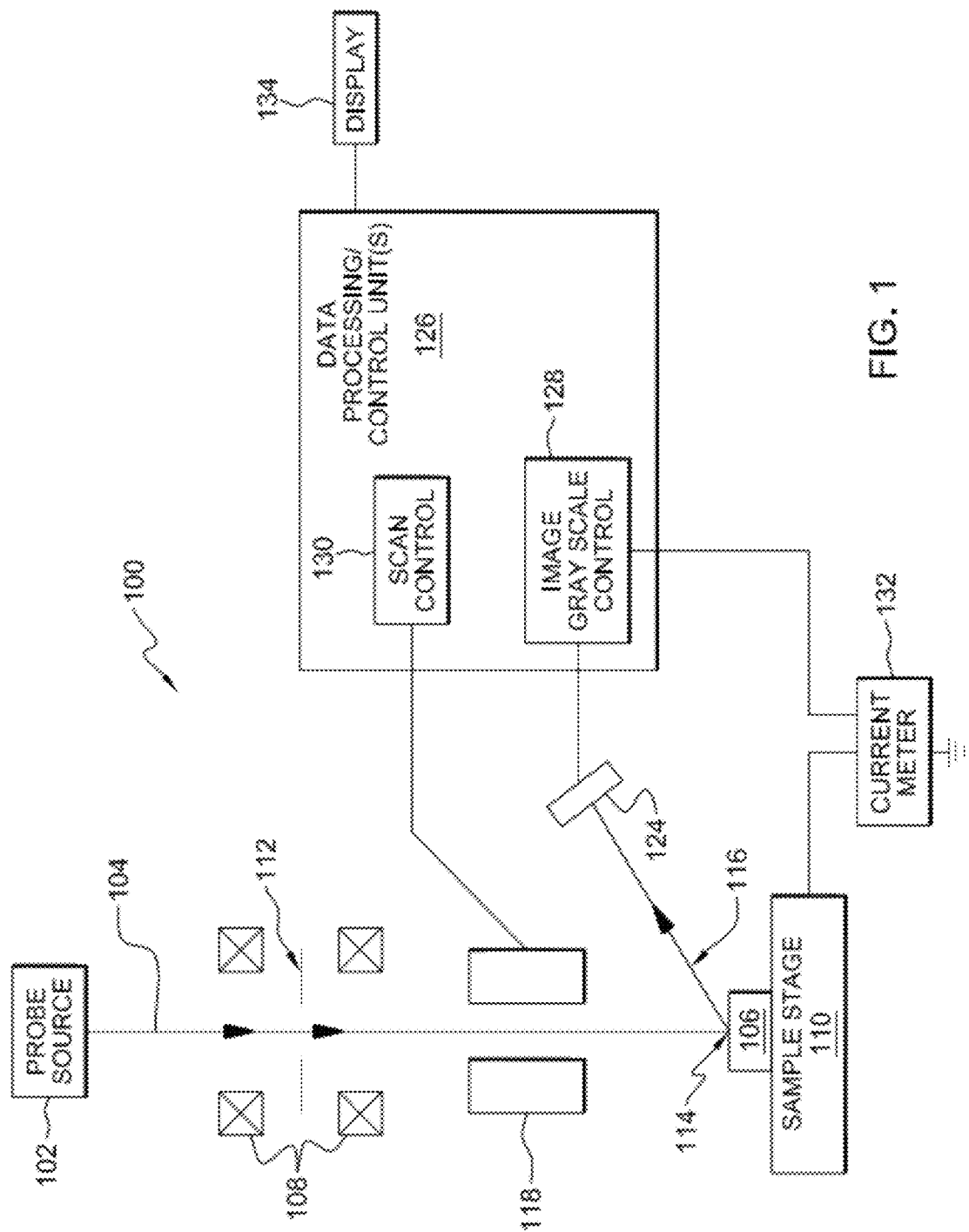
FIG. 1 depicts one example of an imaging device that may incorporate and use one or more aspects of the present invention.

Aspects of the present invention can be used in conjunction with various imaging techniques, including sequential imaging techniques. Sequential imaging involves scanning a probe across a sample object, typically in a series of lines called a raster. At the same time, a signal related to the intensity of an emission (an 'emission intensity') generated by the probe, or the reflected intensity of the probe itself, striking various points of the sample object, may be displayed on a synchronously scanned display.

One example of a sequential imaging technique with which the present invention may be employed is scanning electron microscopy (SEM), where the probing signal is an electron beam and the generated signal typically (though not always) consists of secondary electrons. In SEM, electrons are directed from a source towards a sample. Sources can include a tungsten filament, a lanthanum hexaboride filament, a cold field emitter, or a Schottky emitter, to name a few. In SEM, the electrons are focused to a spot on the surface of a sample by one or more lenses, for example magnetic lenses, which create an electron beam probe. The probe can be scanned over the surface of a sample, for instance by deflection coils. A scan generator can be used to control both the area scanned on the sample and the area on a synchronously scanned display. As the probe dwells at each point on the sample, an emission intensity, such as the intensity of secondary electrons emitted from that point, may be measured, which may then be used to control the intensity of the display.

This is just one example of a sequential imaging technique. There are many other examples of sequential imaging techniques based on, for instance, the use of electrons, ions, or photons as the scanning probe used to generate a broad variety of emitted, reflected or transmitted signals that can be used to control the intensity of the display. For electron probes, these signals, in addition to the secondary electrons mentioned, could be, for instance, backscattered, transmitted or Auger electrons, as well as photons in the visible, near visible, or x-ray spectrum. For ion probes, similar signals can be generated in addition to ions. For photon sources, the signals can be, for instance, photons or electrons. This plethora of probe and signal combinations has given rise to numerous commercially available techniques, all of which can be benefited by the invention. A non-limiting list of examples of techniques that can benefit include: scanning electron microscopy (SEM), scanning transmission electron microscopy (STEM), auger electron microscopy, focused ion beam (FIB), secondary ion mass spectrometers (SIMS), Rutherford backscattering (RBS), proton induced x-ray emission (PIXE), x-ray photoelectron spectroscopy (XPS), and x-ray fluorescence (XRF).

The above techniques are set forth for example purposes, and persons having ordinary skill in the art will recognize that these examples do not limit the applicability of the invention just to the examples provided herein. For instance, aspects of the present invention may be employed in examples involving other imaging techniques.

One example of a device employing sequential imaging is shown in FIG. 1. It should be appreciated that this is provided as just one example of an imaging device that may be employed in conjunction with the present invention.

In FIG. 1, imaging device 100 includes a probe source 102 which generates a probe 104, such as a particle beam of electrons, ions, or photons, directed towards a sample specimen 106. Probe 104 may be focused using one or more lenses 108. Focusing a probe is one way of controlling the probe diameter. As will be explained in further detail below, controlling the probe diameter causes an adjustment to a point spread function associated with the probe, as well as a possible change in the probe current.

Probe diameter may also be controlled by adjusting the vertical position of a sample stage 110. Adjusting the sample stage (e.g. up or down) controls probe diameter because, typically, the probe converges on the specimen at some angle at the point of impact on the sample. The angle at which the probe converges on the sample is affected by a limiting aperture 112, usually placed somewhere in the optical column of the instrument, for instance, in FIG. 1, between lenses 108. The probe current can be controlled by changing various parameters including, for instance, the aperture size or focal length of the lenses.

The position of the probe 104 relative to the sample 106 can be controlled, in one example, by a beam scanning system 118. A beam scanning system 118 may comprise, for instance, in the case of a SEM, a magnetic deflection system. Alternatively or additionally, the beam scanning system may control the position of the probe 104 by mechanical displacement of the sample stage 110, such as by movement of the sample stage in a vertical, horizontal, or other directional plane.

In operation, probe 104 strikes the sample 106 at some point, or spot area, 114, and a signal (emission intensity), 116 is emitted. As examples, the emission intensity 116 may be generated by the impact of the probe 104 on the sample 106, or may be a reflection of part of the incident beam. The emission intensity 116 is then detected by one or more detector(s) 124, which may be tailored to the specific type of signal originating from the sample (for example, electron, ion, x-ray, etc.). The detector(s) 124 may, if necessary, convert the emission intensity 116 into a form suitable for subsequent processing. In the case of an SEM, for example, the conversion may involve a solid state device or a photomultiplier with a voltage output proportional to the strength of the signal. Additionally, it may be desired to measure or image probe current using a current meter 132, which can be used, if needed, to normalize emission intensity data collected by detector(s) 124.

After an emission intensity is detected, it may be input to an input portion of one or more data processing/control unit(s) 126. Data processing/control unit refers generally to any component that may communicate or interact with one or more components of the imaging device to process data and/or control operation of the device. For instance, data processing/control unit(s) may comprise one or more processing systems comprising one or more processors coupled directly or indirectly to one or more memory elements through a system bus. Data processing/control unit(s) typically, though not always, comprise one or more processing units to process data, for instance incoming detected signal intensities for display on a display unit, and/or for carrying out processing operations for automatically controlling various components of the imaging device. In this example, data processing/control units 126 comprise an image gray scale control box 128, and a scan control unit 130. Image gray scale control box 128 may process, in real-time, emission intensities detected by detector(s) 124 (which are in communication with the image gray scale control box 128) to adjust the gray scale and/or black levels for display on one or more display units 134. Additionally, image gray scale control box 128 may be in communication with current meter 132, which may provide information (such as normalization data discussed above) usable by the image gray scale control box 128 when imaging the object for display on the one or more display units 134. Common display units include a cathode ray tube (CRT) or light emitting diode display (LED). The brightness value of each point on the display unit(s) 134 is related to the emission intensity of the signal 116 emitted from the sample. One having ordinary skill in the art would recognize that alternative image control unit(s) may be used in conjunction with or in place of image gray scale control box 128. For instance, one or more RGB control units may be used to create color images instead of grayscale images, for display on a color display.

Scan control unit 130 of the one or more data process/control unit(s) 126 may interact with the beam scanning system 118 to control parameters of the scan, for instance to cause the beam scanning system 118 to reposition the probe on the sample. The scan control unit 130 may also be used to position the coordinates of a display beam on the one or more display unit(s) 134.

The data processing/control unit(s) 126 may optionally be connected to various other components for facilitating aspects of the current invention. For example, data process/control unit(s) 126 may be in communication with the probe source 102, one or more lenses 108, the sample stage 110, aperture 112, the beam scanning system 118 and/or other components of the imaging device or ancillary equipment via one or more other communications paths.

Additionally, the data processing/control units 126 may comprise one or more computers to be used to set key instrument parameters. Such parameters include, but are not limited to, probe energy, scan rates, numbers of pixels in the image, etc. In one example, an operator console (not depicted) may be provided which may comprise various I/O devices to facilitate setting and/or displaying instrument parameters and/or other user interfacing. A non-limiting list of examples of I/O devices includes keyboards, computer mice, touch sensitive displays, joystick controls, knobs, sliders, and displays.

When scanning samples, it is useful to adjust probe size, corresponding to the spot area, or area of the sample being probed by the probe. A useful way to envision the area being probed is as a box of size n×n where n is a positive integer. This area may then be represented as the union of unit squares (pixels) with corner points (i,j), $0 \le i,j \le n$. As will be described further below, in accordance with aspects of the present invention, a spot area of a sample is scanned with a probe current $i_p$ and a probe diameter $d_p$, where $d_p$ is considerably bigger than the feature size (pixel) on the sample.

Figure 2C:
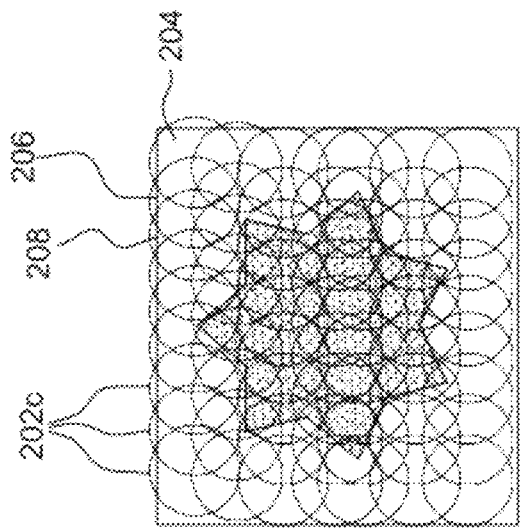
FIGS. 2A-C illustrates beam sampling patterns on a sample as magnification increases for a fixed scanning probe size.
Figure 2B:
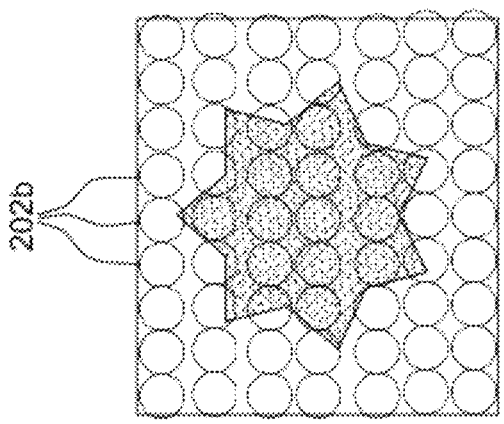
Figure 2A:
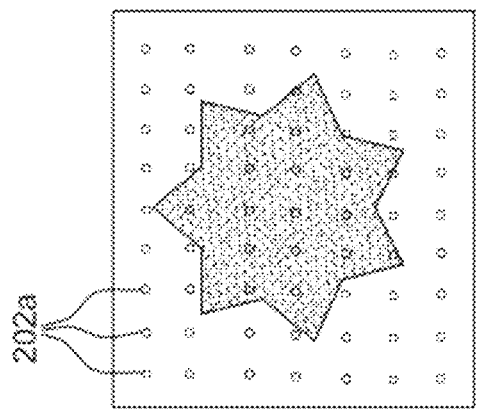

When the size of the probe is larger than the size of the pixel, blurring occurs. FIGS. 2A-C show the beam sampling pattern on the sample as the magnification is increased for a fixed probe size, i.e. a fixed probe diameter. FIG. 2A corresponds to low magnification. As can be seen in FIG. 2A, when the product of the beam diameter and the total number of steps 202a taken along a line is smaller than the total distance scanned along that line, then individual probe area steps 202a will be well-separated, and under-sampling will occur. At some intermediate value of magnification, the probe size will be such that each step will be tangent to the next. In this case, the product of the beam diameter and the number of steps taken along a line is equal to the total distance scanned along that line. This is depicted in FIG. 2B, where probe areas steps 202b are substantially tangent to one another. At high magnification (FIG. 2C), the steps will be begin to overlap and the effect known as oversampling will occur. In this case, the product of the beam diameter and the number of steps will be greater than the total distance scanned. An oversampled image appears blurry on the display because adjacent points on the display will contain information from a range of pixels on the sample. As an example, as depicted in FIG. 2C, a probe of spot area 206, will detect signal coming from spot areas 204 and 208 (and others), because of the overlap of those spot areas.

Oversampling is the result of dispersion of particles (for example, electrons) in the beam such that these particles strike an area larger than the individual features of interest in the sample. While each individual particle is, in fact, striking a very small area of the sample, the emission intensity detected is the sum or composite of all of those particles. In other words, some of the particles in the distribution are striking the feature of interest and others are striking other details of interest nearby. Our challenge is how to tell what part of the signal came from what feature of the sample.

It is known that probes have associated with them a geometric probe profile which is referred to as a point spread function and which describes the distribution of the beam around its center. Point spread functions are usually associated with a bell shaped curve, which is often approximated by a Gaussian shape. Even though a blurry image obtained by oversampling can be described as the convolution of the actual structure with the point spread function, it can be shown that the number of equations that need to be solved to deconvolute the structure using a known point spread function is smaller than the number of unknown values of the signal that would be obtained from the true (deconvoluted) structure.

However, in accordance with aspects of the present invention, accurate images of an area of an object may be obtained using multiple images of the area that have been captured using different point spread functions. This approach can generate sufficient values using known point spread functions to generate deconvolution equations that define sufficient values of the signal strengths emitted from individual picture elements to be solvable to obtain a high resolution image of the object.

Aspects of the current invention will be described according to a "localization principle". This is described in conjunction with FIG. 3, however some important mathematical principles must first be provided.

Consider a function $f(x,y)$ which corresponds to the signal that would be measured if the probe diameter was equal to zero, that is, if all the particles of the beam hit the sample at point (x,y), $0 \le x$, $y \le n$. $f$ is proportional to the probe current and also depends on the efficiency and effective solid angle and position of the detector. We extend $f(x,y)$ defining it to be zero outside of the square of dimensions n×n. We assume that if the probe is targeting the point of origin (0,0), the fraction of the probe current striking the point of the sample at the location (x,y) is given by a point spread function (PSF). This can be represented by $\phi(x,y)$, a non-negative function which satisfies the condition:

$$\int_{\mathcal{R}^2} \phi(x,y) dx dy = 1.$$

If, for example, the shape of the beam is approximately bivariate Gaussian, then the PSF is approximately bivariate Gaussian and is given by:

$$g(x, y) = \frac{1}{2\pi\sqrt{1-\rho^2}\,\sigma_1\sigma_2} e^{-\frac{1}{2(1-\rho^2)}\left[\frac{x^2}{\sigma_1^2} - 2\rho\frac{xy}{\sigma_1\sigma_2} + \frac{y^2}{\sigma_2^2}\right]}.$$

If x and y are independent (and, therefore, the correlation $\rho$ is equal to zero) and $\sigma_1 = \sigma_2$ (an isotropic case), the Gaussian PSF takes the following simple form:

$$G(x, y) = \frac{1}{2\pi\sigma^2} e^{-\frac{x^2+y^2}{2\sigma^2}}.$$

Even though Gaussian point-spreads are frequently viewed as sufficiently accurately describing the PSF associated with a probe, aspects of the present invention work with any PSF, Gaussian or otherwise, so long as it is known or can be accurately approximated.

The signal $s(x,y)$, recorded when the center of the beam is positioned at the point (x,y), is expressed in terms of the functions $f$ and $\phi$ in a convolution form as follows:

$$s(x, y) = \int_{\mathcal{R}^2} f(x+t, y+z)\varphi(t,z) dt dz + \varepsilon(x,y) = f * \tilde{\varphi}(x,y) + \varepsilon(x,y),$$

where $\tilde{\phi}(t,z) = \phi(-t,-z)$, and where $\varepsilon(x,y)$ is a noise reflecting the stochastic nature of the emission and signal collection, since the convolution of two functions $f(x,y)$ and $g(x,y)$ is defined by:

$$f * g(x, y) = \int_{\mathcal{R}^2} f(x-t, y-z) g(t, z) dt dz$$

$$= \int_{\mathcal{R}^2} f(t, z) g(x-z, y-z) dt dz.$$

If $\phi(-t,-z)=\phi(t,z)$, like in the case of a Gaussian PSF, we can express the signal s as:

$$s = f * \phi + \epsilon.$$

In what follows, we assume that this symmetry takes place by default. The PSF function $\phi$ usually decays fast as $\sqrt{x^2+y^2}$ tends to infinity, like it happens in the case of a Gaussian spread. It is common for this reason to think that $\phi$ is compactly supported, that is, that there is a positive $\tau$ such that:

$$\phi(x,y)=0, \text{ if } \max\{|x|,|y|\} > \tau/2. \qquad (1)$$

The minimal number $\tau$ such that (1) is satisfied is called the beam size, or the beam diameter and is denoted by $d_p$.

The justification of the compactness of the PSF support (or, equivalently, the finite beam size) follows from known mathematical properties, i.e. Hölder's inequality, which can be used to show that the error caused by the truncation is decreasing when $\tau \to \infty$, so that if $\tau$ is big enough, the error is negligible.

Following this approach, when speaking of a Gaussian beam of size r, the PSF is given by:

$$G_r(x, y) = \begin{cases} ce^{-\frac{x^2+y^2}{2\sigma^2}} & \text{if } \max\{|x|, |y|\} \le r/2, \\ 0 & \text{otherwise,} \end{cases}$$

where c is the normalizing constant and r is chosen so that the error is small (for instance $r=6\sigma$).

We can represent a scan using a particular probe diameter, $d_p$, as follows:

$$s_{d_p} = f * \phi_{d_p} + \epsilon,$$

meaning that the signal $s_{d_p}$ was obtained from the scan with the Gaussian shape beam of diameter $d_p$ (and, hence, in the Gaussian case, the standard deviation $\sigma=d_p/6$).

To further adjust the model to the realities of imaging devices, such as SEM devices, it should be appreciated that the probe source does not emit particles continuously, but instead, emits particles only when it targets the centers of pixels, i.e. the time spent between pixels is much shorter than the dwell time per pixel. The results of the scan are recorded only for these coordinates (x,y). As a consequence, the original signal $f(x,y)$, point spread function $\phi_{d_p}(x,y)$, and recorded signal $s_{d_p}(x,y)$, are step-functions constant on each pixel. Thus, in fact, all of these functions are represented by matrices $F=[f_{ij}]$, $\Phi_{d_p}=[\phi_{ij}]$ and $S_{d_p}=[s_{ij}]$ of dimensions n×n, $d_p \times d_p$, and $(n+d_p) \times (n+d_p)$, respectively. Thus, the convolution model takes the matrix form:

$$S_{d_p} = F * \Phi_{d_p} + \epsilon, \qquad (2)$$

where $\epsilon=[\epsilon_{ij}]$ is now a random matrix of size $(n+d_p) \times (n+d_p)$ representing the noise.

The actual value of the signal s measured is related to a number of factors including probe current, the dwell time per pixel, the yield of the signal per incident particle, the solid angle defined by the detector and its position, and the efficiency of the detector. The relationship between all of these variables is summed-up in an expression called the threshold equation:

$$i_p \ge \frac{4 * 10^{-18} n}{s_{ij} C^2 t_f}, \qquad (3)$$

where $i_p$ is the probe current, C is the contrast (here $$C \ge \frac{5}{\sqrt{s_{ij}}})$$

known as the Rose Criteria, and $t_f$ is the time to collect one frame, i.e. to detect signals from all of the pixel areas in the frame. When the conditions of equation (3) are met, details in the image will be detectable above the noise providing they are spatially resolvable.

Further, usually, there is no scanning with the center of the probe being outside the sample, that is, in fact, both matrices $S_{d_p}$ and $\epsilon$ have sizes n×n. Assuming this to be the case, relation (3) above does not represent the "true" convolution. Also, it assumes that the signal obtained from the material outside the sample is equal to zero. Nevertheless, if $d_p/2<i,j<n-d_p/2$, we have:

$$S_{ij} = \sum_{k,l=-d_p/2}^{d_p/2} F_{i-k,j-l} \Phi_{kl} + \epsilon_{ij}, \qquad (4)$$

which agrees with relation (2) above. Usually, the size of the sample n is much bigger than the diameter of the beam $d_p$, so that the equation (4) above adequately describes the obtained signal.

Thus, the goal to produce an accurate high-resolution image becomes (see equation (2) above): given the registered signal matrix $S_{d_p}$ and the PSF matrix $\Phi_{d_p}$, find the original signal matrix F.

Returning to the description of our "localization principle", consider a square box B inside the sample, where the box is of size m and is centered at the point $$\left(\frac{i-m}{2}, \frac{j-m}{2}\right).$$

Figure 3:
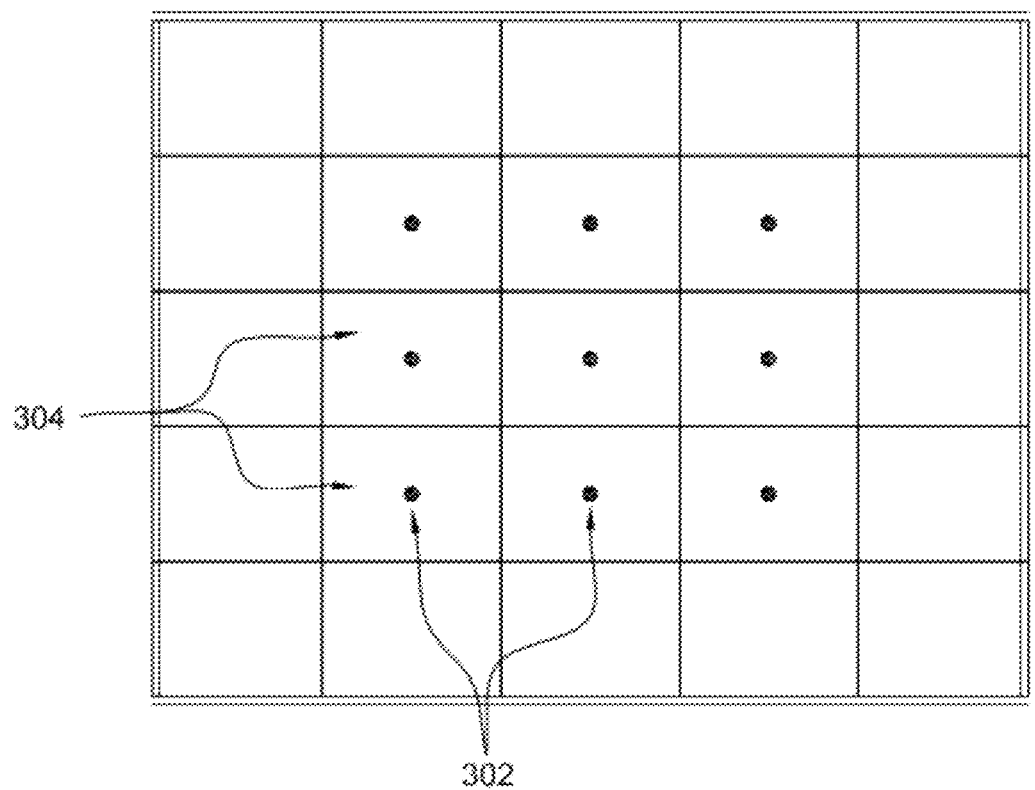
FIG. 3 depicts one example of a reconstruction patch, in accordance with one or more aspects of the present invention.

We can denote this box $B_{ij}(m)$, where $m>d_p$, m being the pixel size and $d_p$ being the diameter of the probe. The number of equations (see equation (4)), above, where only variables $f_{st}$ from $B_{ij}(m)$ are involved is $(m-d_p+1)^2$. FIG. 3 illustrates this concept in the case where m=5, $d_p=3$, and the coordinates of the center of the top right pixel are (i,j). In FIG. 3, dots 302 indicate the centers of pixels 304. A dot at the center of a pixel indicates that a 3 pixel×3 pixel box (corresponding to probe with size $d_p=3$) centered at the pixel lies entirely inside $B_{ij}(5)$. In FIG. 3, nine dots indicate the nine pixels of $B_{ij}(5)$ for which a 3 pixel×3 pixel box centered at the respective pixel lies entirely inside $B_{ij}(5)$. The number of dots, nine, can be computed using the formula above, $(m-d_p+1)^2=(5-3+1)^2$.

Thus, for every scan with the diameter of the beam less than or equal to m, we have a non-trivial number of equations (see equation (4)), above, where all the variables involved come from the box $B_{ij}(m)$. Recall that these variables correspond to the intensity of an emission from a particular pixel inside box $B_{ij}(m)$. It follows from this that when the diameter of the beam changes from r to m, the total number of equations where no other variables than those belonging to $B_{ij}(m)$ are involved is of order $m^3$, while the number of variables inside $B_{ij}(m)$ is equal to $m^2$. Therefore, given probe diameter r starting with some m, the number of equations where only variables from $B_{ij}(m)$ participate exceeds the number of these variables, and, therefore, choosing $m^2$ of these equations, we can find all $f_{ij}$ which come from $B_{ij}(m)$. This allows us to reconstruct the original signal inside the box $B_{ij}(m)$.

If the size m exceeds a certain critical number, so that the number of equations is no less that the number of variables, we call any box of this size a "reconstruction patch".

The critical number depends on r, the minimal diameter of the beam which our imaging device can provide. We can prove that it is equal to one plus the integral part of the positive root of the following cubic equation, which we'll term the characteristic equation (one can verify that this equation as an equation in x has only one positive root):

$$2x^3-3x^2(2r-1)+x(5r^2-15r+11)-2r^3+9r^2-13r+6=0.$$

A direct substitution shows that the critical number does not exceed 2r. For example, if r=20, the critical number, $\hat{m}(r)$, is $\hat{m}(20)=36$. Therefore, we can use a reconstruction patch of size m=36 to reconstruct every patch of size 36×36 pixels. Thus, the number of equations (and variables) of the corresponding system is $36^2=1296$, which may be solved quickly by standard mathematical software, such as, for instance, the MATLAB® computational environment. Once the equations are solved and the variables known, an enhanced accurate image of the 36×36 pixel area of the object can be generated using these variables, and, again, by using only probe sizes larger than the size of each pixel. This reconstruction may be repeated for other reconstruction patches of the sample to cover an entire area of the sample that is of particular interest. In this example, an entire area of a sample may be imaged in patches of size 36×36 pixels.

As can be seen from the above, this "localization principle" enables, using multiple sizes scans producing blurred (convoluted) signals, the construction of an image of an area of an object in a sequence of reconstruction patches. The size m of each reconstruction patch can be any number which exceeds the critical number.

Using this method can improve the resolution r times, however this is not a limit on the extent to which resolution may be improved. For instance, further resolution increase may be achieved by adjusting (i.e. decreasing) the step increment size of the probe position on the sample (e.g. distance between spot areas probed), which correlates to increasing the number of pixels within a reconstruction patch.

When the size of a reconstruction patch is equal to the critical number, a number of scans that can produce sufficient values for reconstructing the image is equal to the critical number minus r, the minimum probe diameter of the imaging device. In the example above where r=20 and the critical number=36, the number of scans used for a reconstruction was equal to 16 (i.e. 36−20=16), corresponding to a scan using each probe diameter from 20 to 35. It may, however, be desirable to decrease this number of scans in order to decrease the amount of time necessary to image the object. This is preferred because imaging devices, such as those described herein, may, after prolonged use, experience various undesirable environmental or design effects such as drift or contamination. Additionally, scans may adversely affect the various properties of the sample being scanned, such as is the case of an organic sample where exposure to radiation levels may damage or destroy the sample.

One option to decrease the number of scans is to increase the size of the patch, which results in an excess of the number of equations over the number of variables. This creates an opportunity to omit some scans that would otherwise be required to obtain the signals necessary to accurately reconstruct the patch. At the same time, the increase of the size of the patch leads to a fast growth of the number of variables involved, and, therefore, to a rapidly growing reconstruction time for each individual patch and, consequently, the whole sample area of interest.

Depending on equipment, this approach may be acceptable. However, in another aspect of the invention, an optimal balance may be found between the increasing size of the patch and the decreasing number of necessary scans. To find this optimal balance, the following extremal problem is presented.

As above, we denote the minimal possible size of the beam diameter as r. Also, denote the time of a scan by $t(\rho)$ when the diameter of the beam is equal to $\rho$. A set of scans with beam sizes $\rho_1, \ldots, \rho_k$, will yield a total scanning time, given by:

$$t_{sc}(\rho_1, \ldots, \rho_k) = \sum_{j=1}^{k} t(\rho_j).$$

Given $m \geq \hat{m}(r)$, let $t_s(m)$ denote the computational time necessary for forming the matrix of the system of equations and solving the system of $m^2$ equations in $m^2$ variables. The numbers for variables m and s are obtainable from experiments using standard mathematical software, such as, for instance, the MATLAB® computational environment. The total reconstruction time using patches of size m×m is now given by:

$$T(\rho_1, \ldots, \rho_k; m) t_{sc}(\rho_1, \ldots \rho_k) + \frac{n^2}{m^2} t_s(m).$$

It can be seen that that $T(\bullet)$ is a fast growing function.

Suppose also that $d(\rho)$ denotes the cumulative impairment inflicted by environmental and device effects mentioned above, such as contamination, drift, radiation, etc. for a $\rho$-scan of the sample. c is then a cost function. The total impairment caused by $\rho_1\text{-}, \ldots, \rho_k$-scans is given by:

$$D(\rho_1, \ldots, \rho_k) = \sum_{j=1}^{k} c(\rho_k). \tag{5}$$

We pose the following extremal problem:

$$T(\rho_1, \ldots, \rho_k; k, m) \to \min \bigg/ \begin{array}{c} \sum_{j=1}^{k}(m-\rho_j+1)^2 \geq m^2 \\ D(\rho_1, \ldots, \rho_k) \leq D_{max} \\ \hat{m}(r) \leq m \leq M, \end{array} \tag{6}$$

where $D_{max}$ is the maximal admissible impairment level, $\hat{m}(r)$ is the critical number, and M is an a priori upper bound for the size of the patch which indicates that any further increase of this size is not practical.

Problem (6) is a non-linear discrete mathematical programming problem. The solution to problem (6) gives optimal values of the size of the reconstruction patch and a best set of necessary scans, for instance the optimal number of scans and probe sizes, to use in generating the enhanced image.

Finding a solution to problem (6) above can be facilitated by using any admissible point $(\rho_1, \ldots, \rho_k; k, m)$ which is sufficiently close to the point of extremum. Finding such an approximation may be achieved using, for instance, spline interpolation and gradient methods.

As an example, when r=20 and the cost function is $T(\rho_1, \ldots, \rho_k; m)$ (no scan damage), it can be found that m=43, and the number k of necessary scans is 6, with scans of probe sizes 20, 21, 23, 24, 26 and 27 pixels. Using these parameters, the reconstruction time for one 43 pixel×43 pixel patch was less than 2 minutes using a computer of average processing power.

Based on problem (6) above, it is possible to prove that when m≤100, the optimal number of necessary scans does not exceed 10, and that the number of necessary scans is usually around 5 or 6.

With the above in mind, a method for generating an image will be described with reference to FIGS. 4-6.

Figure 4:
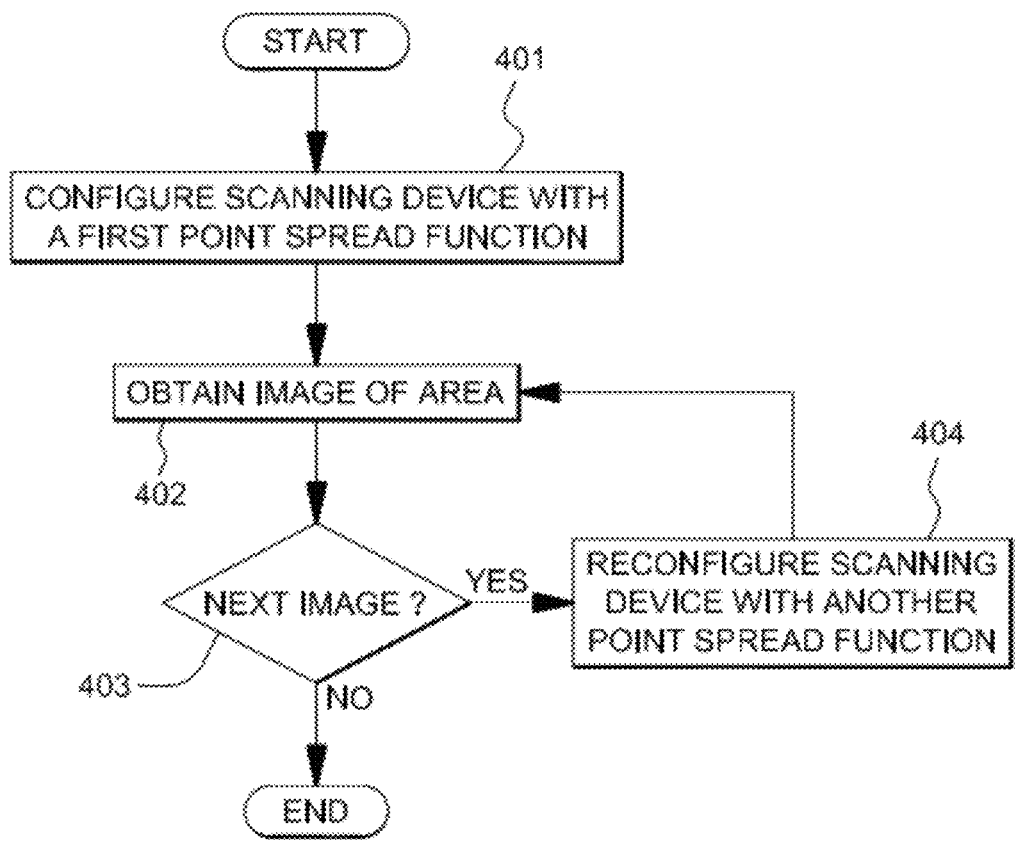
FIG. 4 depicts one process for imaging an area of an object, in accordance with one or more aspects of the present invention.

FIG. 4 depicts one method for imaging an area of an object using multiple point spread functions. As described above, the spatial distribution of the probe is described by separate matrix $\Phi_p$, which is the point spread function associated with the probe. As an overview of the method in FIG. 4, the point spread matrix may be incremented to create a series of images, $S_p$, with each image of the series of images corresponding to the convolution of a different $\Phi_p$ with the sample matrix. Thus, in STEP 401 imaging commences by, for instance, configuring the imaging device with a first point spread function. Then, in STEP 402, an image of the area of the object (or a portion thereof), is obtained using the imaging device. This is described in greater detail below with respect to FIG. 5. After obtaining an image of the area, inquiry 403 determines whether a next image of the area is to be obtained using a different point spread function. If so, the imaging device may be reconfigured with another point spread function, STEP 404. This may be accomplished by, for example, changing a sample stage position of the object, and/or by changing a focus of the probe. Alternatively or additionally, this may be accomplished by varying a focal length of a condenser and objective lens of the imaging device. A change in the point spread function can change the size of the probe to change the size of the area on the object that is covered by the probe (spot size). The size of the probe may be changed to correspond to the desired probe sizes for the reconstruction patch, as described above. The size of the probe may be initially selected such that it produces a spot size on the sample equal to or larger than the minimum spot size achievable with the probe device. This size will generally be larger than one pixel, so that the probe will cover multiple pixels to produce a composite signal of multiple signals from the multiple pixels.

Varying the point spread function (e.g. to increase probe size) forces the sample matrix to a larger size. This process of incrementing the size of the sample matrix and obtaining the resulting image may be repeated for multiple passes. For instance, after the device is reconfigured with another point spread function, STEP 404, the imaging process may be repeated to obtain another image of the area (or a portion thereof) STEP 402, so as to produce another image obtained using a different point spread function. The number of images (and their associated point spread functions) may be determined by, for example, solving the extremal problem (6) presented above to determine the "best set" of necessary scans. When there are no further images to obtain, inquiry 403 is answered in the negative and the process of imaging the area of the object ends.

Figure 5:
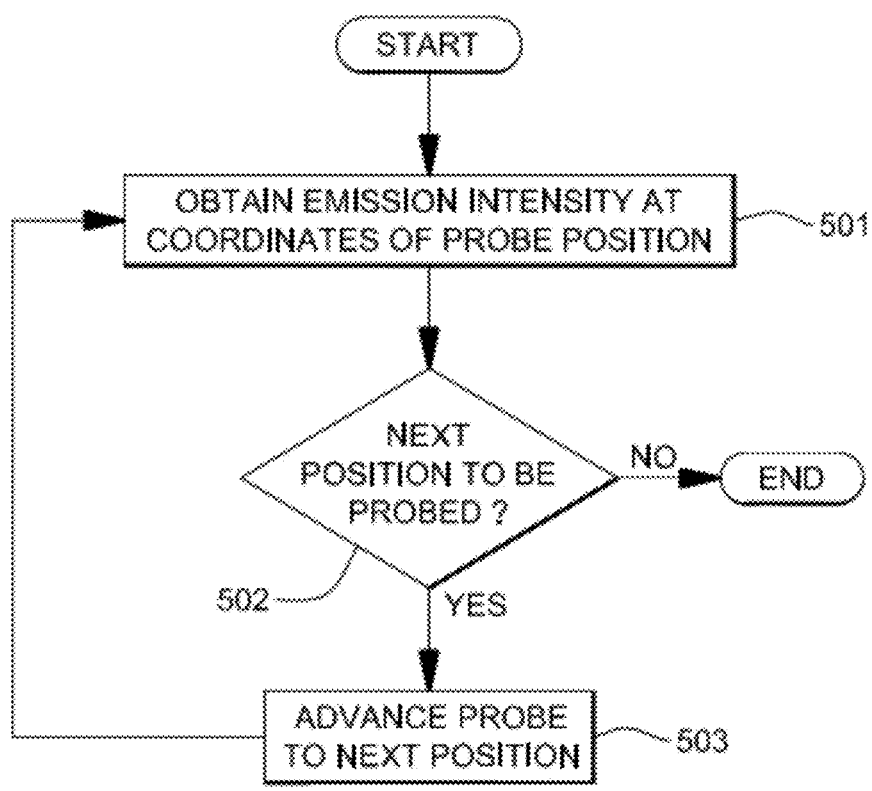
FIG. 5 depicts one process for obtaining an image of an area of an object, in accordance with one or more aspects of the present invention.

FIG. 5 depicts one method of obtaining an image of an area of an object. As noted above, this area can be termed a sample matrix and can be defined by Cartesian coordinates (i.e., x and y coordinate system in the plane of the sample). The sample matrix can be thought of as a set of discrete picture elements, or pixels, each one specified by coordinates i and j. The probe of the imaging device is initially positioned at a coordinate position of the area. Thus, the process begins at STEP 501 with a signal $s_{ij}$ from a point whose coordinates on the sample are i and j is obtained. In one embodiment, the starting coordinate may be where i, j=1, corresponding to a corner of the area to be imaged. Each signal measurement, $s_{ij}$, may result from the detection of at least a maximum signal produced by a chosen number of emitted particles. The number may be chosen based on, for example, statistical considerations such that there will be less than a particular variation of signal strength measurements for a particular percentage of the time if the measurement is repeated. In one embodiment, this number chosen is 10,000 incident beam particles, which yields a less than 2% variation of signal strength measurements 95% of the time if the measurement is repeated.

Once this measurement is made, it is determined whether a next position in the area of the object is to be probed, STEP 502. If so, the probe is advanced (this is called a step) to a new position in STEP 503, for instance an adjacent position at some increment on the two dimensional grid of the sample surface. The probe step increment size may be equal to a predetermined fraction of the initial probe diameter. The probe step increment size, rather than the probe diameter itself, is what may determine the resolution of the final reconstructed image. A typical probe step increment size is 1/20 to 1/5 the probe diameter, however other values may be used.

The probe position may be advanced in a set of steps until individual measurements for all desired spot areas of the area of the object have been obtained. In one embodiment, the total matrix $S_{d_p}$ is obtained, however, it need not be the case that a signal $s_{ij}$ be obtained for every i,j of the area. When emission intensities from all desired spot area have been obtained, inquiry 502 is answered in the negative and the process ends.

Figure 6:
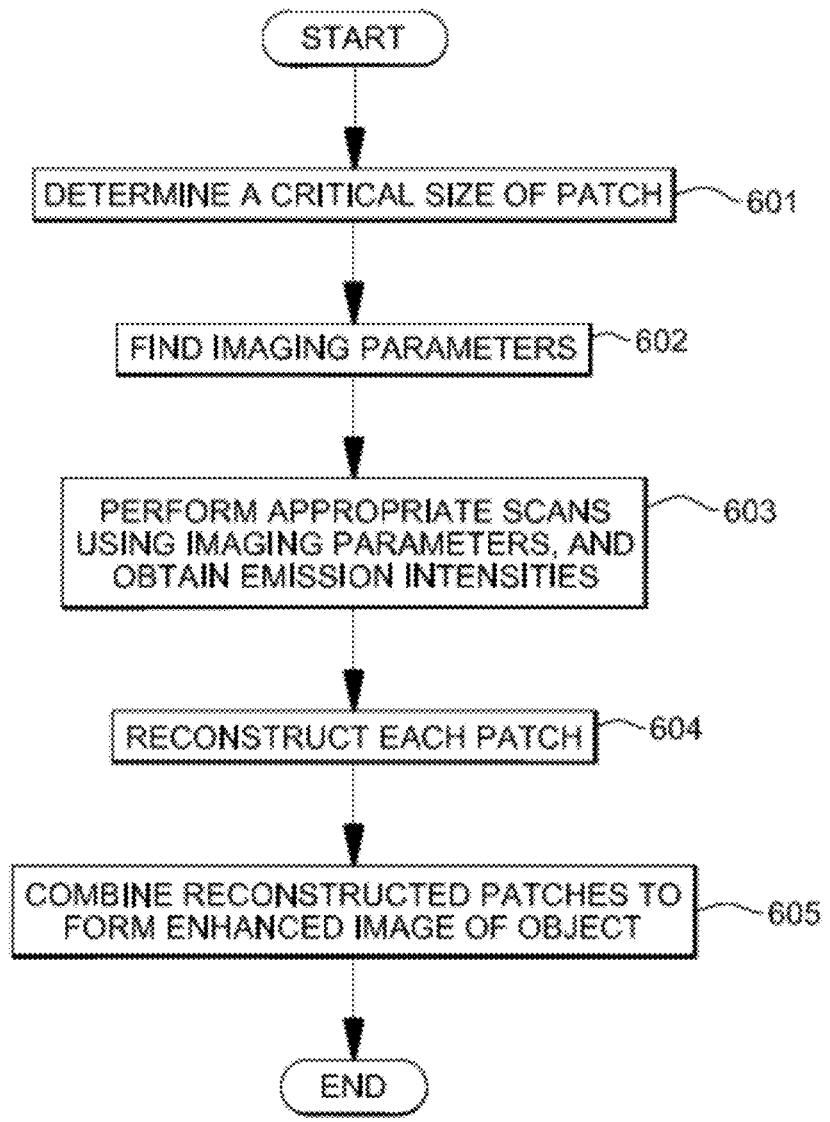
FIG. 6 depicts one process for generating an image of an object, in accordance with one or more aspects of the present invention.

One embodiment of a method for generating an enhanced image is depicted in FIG. 6. In one example, a data processing/control unit(s) as described above may perform the method to facilitate one or more aspects of the present invention.

First, given r (the minimum probe size as determined by the imaging device), the critical size of the patch, $\hat{m}(r)$, and M, the upper bound for the size of the patch (see above) can be determined, STEP 601. Next, we approximate the extremal vector $(\rho_1, \ldots, \rho_k; k, m)$ of problem (6) and find acceptable imaging parameters which include the size of the reconstruction patch, the number of scans to perform, and the spot sizes to use for each scan, STEP 602. Then, the chosen scans may be performed, such as is described above, and the emission intensities obtained can be stored in a matrix form, STEP 603. Using this, the area of interest is covered with approximation patches, and for each patch, the matrix of the system is formed and the obtained signal intensities are used to reconstruct each patch, STEP 604. For instance, a system of deconvolution equations may be generated and solved to determine the intensity of emission from each pixel of the reconstruction patch. Then, each reconstruction patch may be reconstructed from the determined emission intensities. This may be repeated for the multiple reconstruction patches of the object.

Then, the reconstructed patches may be combined to form an enhanced image of the entire area of the sample covered, STEP 605.

Figure 7A:
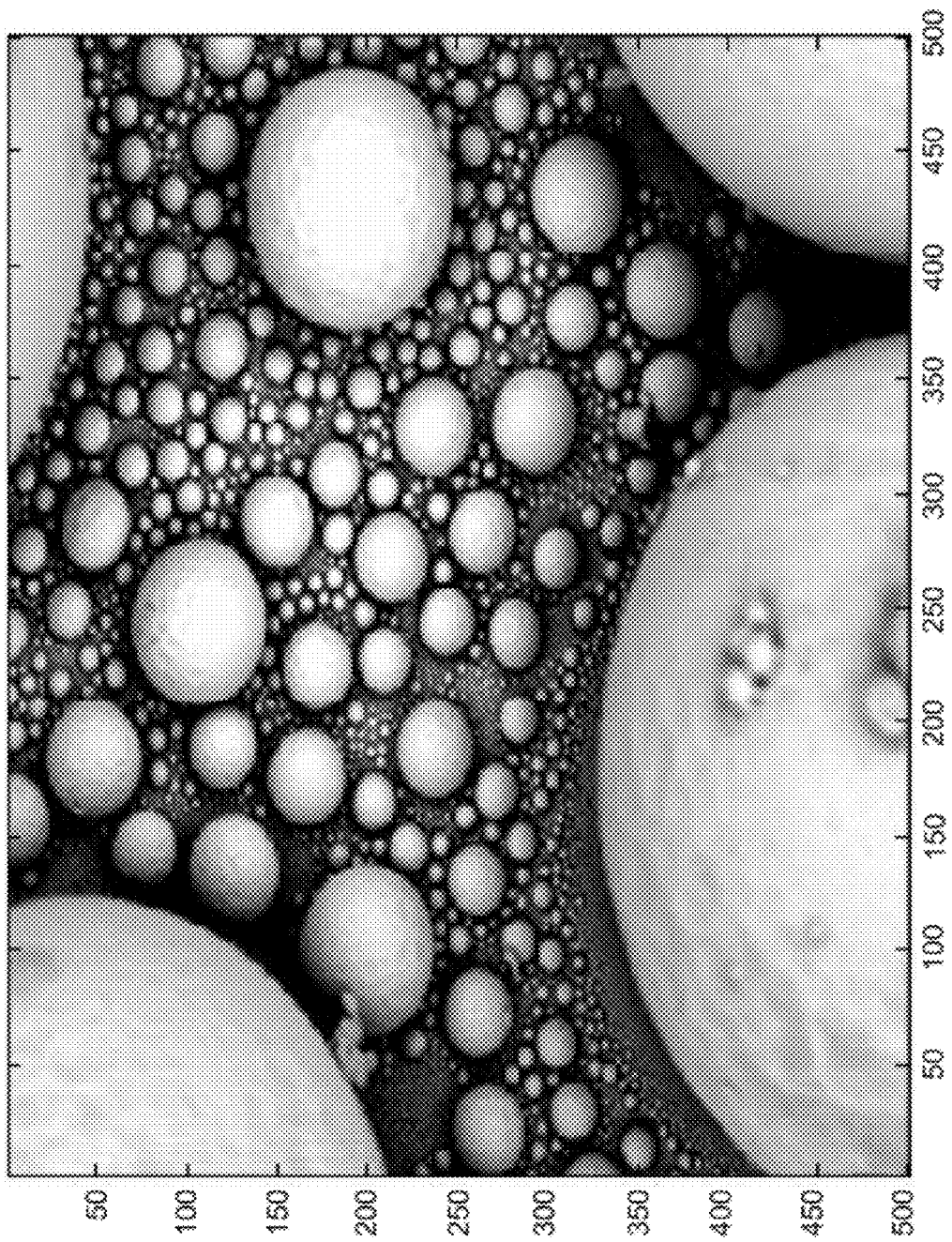
FIGS. 7A-7C illustrates an example in which one or more aspects of the present invention are employed to generate an image of an object.
Figure 7B:
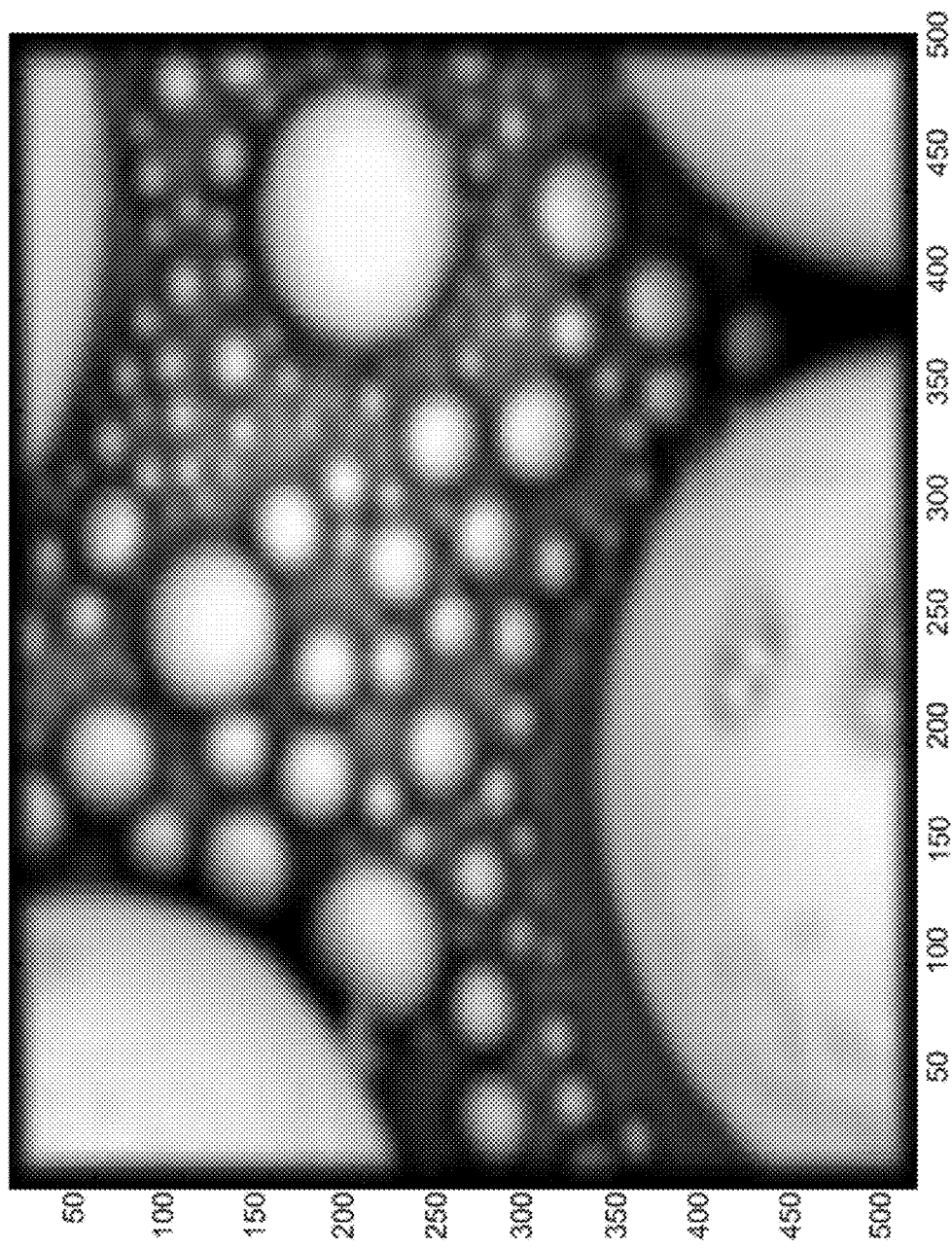
Figure 7C:
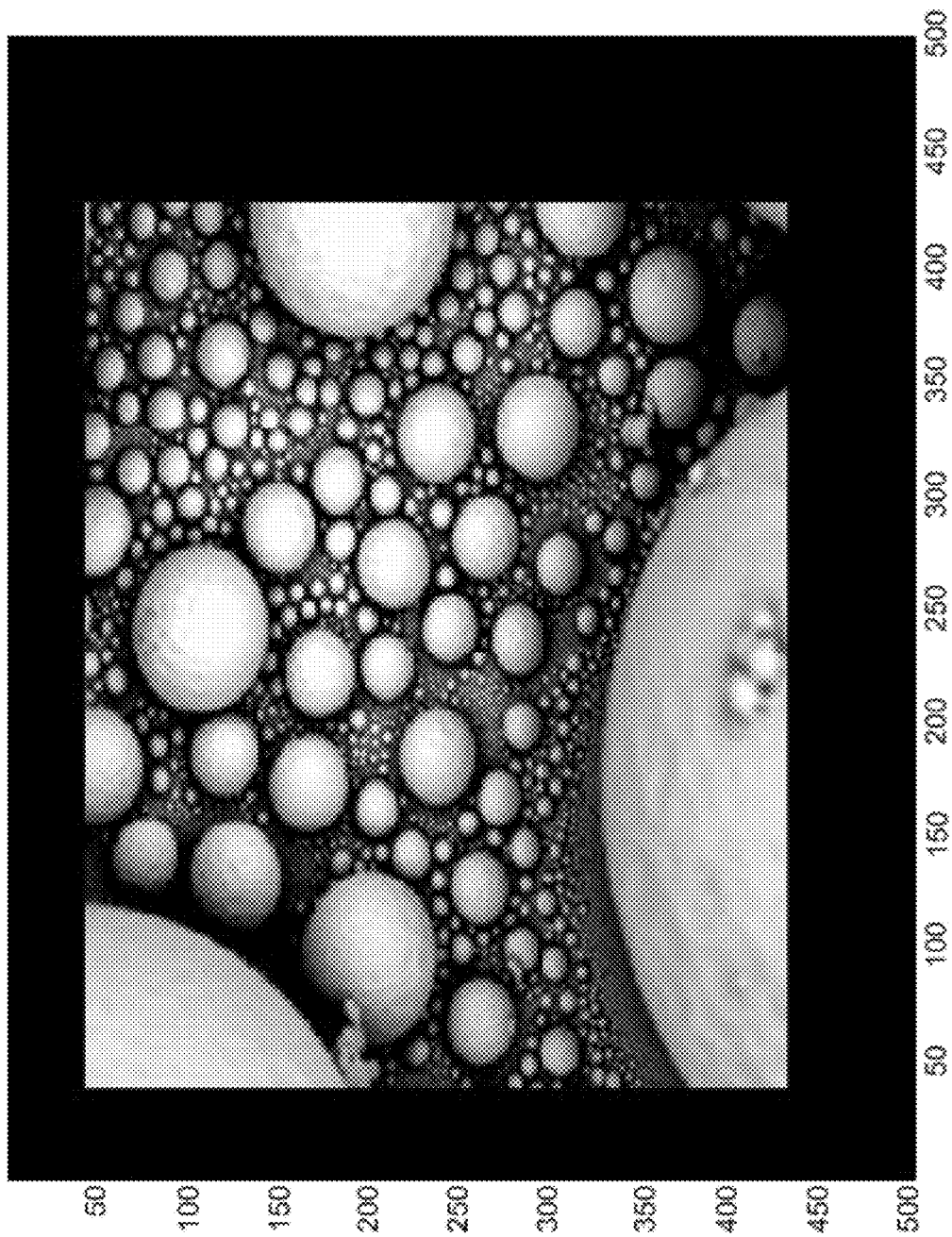

FIGS. 7A-7C illustrate an example in which the method described above is employed to generate an image of an object. FIG. 7A depicts an image having pixel level resolution, and represents the image obtained when the point spread function of the probe simply covered each pixel individually on the sample. FIG. 7A is provided as a reference image to understand the example. FIG. 7B is a blurry image formed by purposely convoluting the image in FIG. 7A with a 20 pixel× 20 pixel point spread function. FIG. 7B therefore represents an image that experiences blurring due to oversampling, i.e. an image that would be obtained if the probe coverage area was larger than the pixel size. The sample area size in FIG. 7B is 512×512 pixels. Since FIG. 7B is convoluted with a 20×20 matrix, minimum probe size r=20. Using the above equations (5) and (6), the cost function is computed and the number of necessary scans was found to be equal to 6, with sizes needed of 20, 21, 23, 24, 26 and 27 pixels. In other words, these values provide a good approximation of the absolute minimum, using problem (6) above. Again, finding such an approximation may be achieved using, for instance, spline interpolation and gradient methods.

Using data obtained with scans according to these parameters, an enhanced image is generated for each reconstruction patch of size 43 pixels×43 pixels, in this example. The enhanced images (of each reconstruction patch) can be combined together to generate an image of the sample area of the object. FIG. 7C depicts a reconstructed image of the sample area of the object. The accuracy of FIG. 7C can be seen by comparing FIG. 7C with FIG. 7A, the reference image, which, again, is the image that would be obtained had the point spread function of the probe simply covered each pixel individually on the sample. The comparison between FIG. 7A and FIG. 7C reveals a quality image of the area of the object using non-Gaussian point-spreads (we used uniform point-spreads instead) to obtain a result similar to that depicted in FIG. 7A. Thus the image in 7C is an enhanced image of FIG. 7B and is what would be obtained, using aspects of the present invention, in a well behaved instrument free of, for instance, environmental and mechanical effects such as vibrations, stray fields, contamination and other possible lens aberrations or distortions that would cause a departure from Gaussian behavior (in the case of Gaussian spreads).

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer program product may include, for instance, one or more computer readable storage media to store computer readable program code means or logic thereon to provide and facilitate one or more aspects of the present invention.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing units or apparatuses, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing units or apparatuses, or other devices to cause a series of operational steps to be performed on the computer, other programmable units or apparatuses or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

As used herein, the term obtaining includes, but is not limited to, receiving, being provided, retrieving, determining, accessing, etc.

Described herein is a method, apparatus, and computer program product for generating enhanced resolution images of an object. Embodiments of the invention provide fine detail resolution while preserving distinguishable levels of contrast and low signal to noise ratios. The invention advantageously overcomes the need to continually decrease probe sizes when desiring to produce an accurate high-resolution image of finer detail. High resolution images are achieved without a need for extremely small and expensive probe sizes which require additional care and expertise to maintain, and which may be available only in relatively expensive equipment. Additionally, the invention may be employed in conjunction with existing imaging devices to enhance the capabilities thereof to generate accurate enhanced images. For instance, limits imposed on the resolution of existing scanning devices due to minimum probe sizes thereof may be exceeded by employing one or more aspects of the current invention, thus resulting in significant cost savings to produce images of higher resolution.

Although embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method of generating an image, the method comprising:
    obtaining images of an area of an object generated using a probe having a probe size greater than or equal to a minimum probe size, wherein obtaining the images comprises configuring the probe with multiple different point spread functions each associated with a respective probe size, wherein the probe is configured with a first point spread function of the multiple different point spread functions, and a first set of images of the obtained images are obtained with the probe having the first point spread function, and the probe is reconfigured with a second point spread function of the multiple different point spread functions, and a second set of images of the obtained images are obtained with the probe having the second point spread function, wherein a point spread function of the multiple different point spread functions is associated with the minimum probe size, and wherein the obtained images comprise one or more convolutions, of a structure of the object within the imaged area of the object, with the multiple point spread functions with which the probe was configured to obtain the images; and
    generating from the obtained images an enhanced image having a higher resolution than that provided by the point spread function associated with the minimum probe size, the generating comprising determining, based on the obtained images and at least some of the multiple different point spread functions with which the probe was configured and used to obtain images of the multiple images, an emission intensity emitted from a pixel area of the area of the object, the determining deconvoluting at least a portion of the structure of the object corresponding to the pixel area, wherein the generated enhanced image comprises a representation of the emission intensity emitted from the pixel area of the area of the object, the pixel area being smaller than the minimum probe size.

2. The method of claim 1, wherein the images of the area of the object comprise multiple emission intensities generated using the probe.

3. The method of claim 1, wherein the obtaining comprises scanning the area of the object using the probe to generate multiple emission intensities, and wherein the multiple emission intensities are emitted from the area of the object.

4. The method of claim 3, wherein the scanning comprises positioning the probe over multiple spot areas of the area of the object, and wherein each emission intensity of the generated multiple emission intensities is emitted from a respective spot area of the multiple spot areas of the area of the object.

5. The method of claim 3, wherein the obtaining further comprises detecting the multiple emission intensities.

6. The method of claim 5, wherein the scanning the area of the object is performed using a scanning device comprising a probe source providing the probe.

7. The method of claim 1, wherein the reconfiguring changes a coverage area size of the object intersected by the probe when scanning the area of the object.

8. The method of claim 1, wherein the reconfiguring comprises at least one of: changing a sample stage position of the object, and changing a focus of the probe.

9. The method of claim 1, wherein the reconfiguring comprises varying a focal length of a condenser and/or an objective lens of the scanning device.

10. The method of claim 1, wherein generating the enhanced image further comprises generating, based on the obtained images and at least some of the multiple different point spread functions, multiple equations describing emission intensity contribution of the pixel area to at least one image of the images of the area of the object, the multiple equations comprising multiple unknowns, wherein a number of equations, of the multiple equations, contributed based on the second set of images obtained by reconfiguring the probe to have the second point spread function, is greater than a number of unknowns, of the multiple unknowns, contributed by the contributed number of equations.

11. The method of claim 10, wherein the determining comprises solving at least one equation of the multiple equations to compute the emission intensity emitted from the pixel area.

12. The method of claim 10, wherein the multiple equations comprise a system of equations comprising at least as many equations as the multiple unknowns, and wherein the determining further comprises solving the system of equations.

13. The method of claim 1, wherein generating the enhanced image further comprises determining multiple other emission intensities emitted from multiple other pixel areas of the area of the object, the determining the multiple other emission intensities deconvoluting other portions of the structure of the object corresponding to the multiple other pixel areas pixel area, the multiple pixel areas of the area of the object being smaller than the minimum probe size.

14. The method of claim 13, wherein the generating the enhanced image further comprises combining the determined emission intensity of the pixel area and the determined multiple other emission intensities of the multiple other pixel areas to generate the enhanced image, and wherein the enhanced image is an image of the area of the object, the area being the size of the minimum probe size.

15. The method of claim 14, further comprising repeating the obtaining and generating to generate at least one other image of at least one other area of the object.

16. The method of claim 15, further comprising combining the generated image of the area of the object and the generated at least one other image to produce an image of the object.

17. The method of claim 1, wherein the probe comprises a focused particle beam, the focused particle beam comprising electrons, photons, ions, or uncharged particles.

18. An apparatus for generating an enhanced image, the apparatus comprising:
  an input portion for obtaining emission intensities corresponding to intensities of emissions from an area of an object, the emission intensities emitted when the area of the object is scanned using a scanning probe having a probe size greater than or equal to a minimum probe size, the emission intensities obtained by configuring the probe with multiple different point spread functions each associated with a respective probe size, wherein the probe is configured with a first point spread function of the multiple different point spread functions, and a first set of emission intensities of the obtained emission intensities are obtained with the probe having the first point spread function, and the probe is reconfigured with a second point spread function of the multiple different point spread functions, and a second set of emission intensities of the obtained emission intensities are obtained with the probe having the second point spread function, wherein a point spread function of the multiple different point spread functions is associated with the minimum probe size, and wherein the obtained emission intensities comprise one or more convolutions, of a structure of the object within the scanned area of the object, with the multiple point spread functions with which the probe was configured to obtain the emission intensities; and
  a processor for generating from the obtained emission intensities, an enhanced image of the area of the object having a higher resolution that that provided by the point spread function associated with the minimum probe size, the generating comprising determining, based on the obtained emission intensities and at least some of the multiple different point spread functions with which the probe was configured and used to obtain emission intensities of the multiple emission intensities, an emission intensity emitted from a pixel area of the area of the object, the determining deconvoluting at least a portion of the structure of the object corresponding to the pixel area, wherein the generated enhanced image comprises a representation of the emission intensity emitted from the pixel area of the object, the pixel area being smaller than the minimum probe size.

19. The apparatus of claim 18, wherein the apparatus further comprises an imaging device for generating the emission intensities.

20. The apparatus of claim 19, wherein the imaging device comprises a beam source for generating the scanning probe, and a detector for detecting the emission intensities emitted from the area of the object.

21. An apparatus for imaging an object, the apparatus comprising:
  a probe source generating a probe and scanning the object with the probe configured with multiple different probe sizes each associated with a respective point spread function, wherein the probe is configured with a first probe size of the multiple different probe sizes and the probe is reconfigured with a second probe size of the multiple different probe sizes, and wherein a minimum probe size of the multiple different probe sizes is associated with a point spread function;
  a detector for detecting signals emitted from an area of the object when scanned using the probe configured with the multiple different probe sizes, wherein the detector detects a first set of signals emitted from the area of the object when scanned with the probe having the first probe size and a second set of signals emitted from the area of the object when scanned with the probe having the second probe size, the detected signals comprising one or more convolutions, of a structure of the object within the scanned area of the object, with the point spread functions associated with the multiple different probe sizes with which the probe was configured to scan the object; and
  a processor for determining, based on the first set of detected signals, the second set of detected signals, and the point spread functions associated with the multiple different probe sizes, at least one signal emitted from a pixel area of the object, the determining deconvoluting at least a portion of the structure of the object corresponding to the pixel area, and for generating, using the determined signal emitted from the pixel area, an enhanced image having a higher resolution than that provided by the point spread function associated with the minimum probe size, the generated enhanced image comprising a representation of the at least one signal emitted from the pixel area of the object, and the pixel area being smaller than the minimum probe size.

22. A computer program product for generating an image of an object, the computer program product comprising:
  a non-transitory computer readable storage medium readable by a processing circuit and storing instructions for execution by the processing circuit for performing a method comprising:
  obtaining images of an area of an object generated using a probe having a probe size greater than or equal to a minimum probe size, wherein obtaining the images comprises configuring the probe with multiple different point spread functions each associated with a respective probe size, wherein the probe is configured with a first point spread function of the multiple different point spread functions, and a first set of images of the obtained images are obtained with the probe having the first point spread function, and the probe is reconfigured with a second point spread function of the multiple different point spread functions, and a second set of images of the obtained images are obtained with the probe having the second point spread function, wherein a point spread function of the multiple different point spread functions is associated with the minimum probe size, and wherein the obtained images comprise one or more convolutions, of a structure of the object within the imaged area of the object, with the multiple point spread functions with which the probe was configured to obtain the images; and generating from the obtained images an enhanced image having a higher resolution than that provided by the point spread function associated with the minimum probe size, the generating comprising determining, based on the obtained images and at least some of the multiple different point spread functions with which the probe was configured and used to obtain images of the multiple images, an emission intensity emitted from a pixel area of the area of the object, the determining deconvoluting at least a portion of the structure of the object corresponding to the pixel area, wherein the generated enhanced image comprises a representation of the emission intensity emitted from the pixel area of the area of the object, the pixel area being smaller than the minimum probe size.

* * * * *